(12) United States Patent
Jacksier et al.

(10) Patent No.: US 7,156,225 B2
(45) Date of Patent: Jan. 2, 2007

(54) REDUCED MOISTURE COMPOSITIONS COMPRISING AN ACID GAS AND A MATRIX GAS, ARTICLES OF MANUFACTURE COMPRISING SAID COMPOSITIONS, AND PROCESSES FOR MANUFACTURING SAME

(75) Inventors: Tracey Jacksier, Lisle, IL (US); Robert Benesch, Clarendon Hills, IL (US); John Kuhn, Houston, TX (US)

(73) Assignee: American Air Liquide, Inc., Houston, TX (US)

( * ) Notice: Subject to any disclaimer, the term of this patent is extended or adjusted under 35 U.S.C. 154(b) by 0 days.

(21) Appl. No.: 11/064,335

(22) Filed: Feb. 22, 2005

(65) Prior Publication Data
US 2005/0150779 A1 Jul. 14, 2005

Related U.S. Application Data

(62) Division of application No. 10/157,468, filed on May 29, 2002, now abandoned.

(51) Int. Cl.
*B65D 85/00* (2006.01)
(52) U.S. Cl. ....................................................... 206/0.6
(58) Field of Classification Search ................ 252/372; 206/0.6
See application file for complete search history.

(56) References Cited

U.S. PATENT DOCUMENTS

| 2,451,915 A | 10/1948 | Buresh |
| 2,700,188 A | 1/1955 | Buresh et al. |
| 2,703,441 A | 3/1955 | Langdon et al. |
| 2,744,294 A | 5/1956 | Buresh et al. |
| 2,882,243 A | 4/1959 | Milton |
| 2,882,244 A | 4/1959 | Milton |
| 2,950,962 A | 8/1960 | Carlson et al. |
| 2,958,593 A | 11/1960 | Hoover et al. |
| 2,972,527 A | 2/1961 | Upton, Jr. |
| 2,991,151 A | 7/1961 | Breck et al. |
| 2,995,423 A | 8/1961 | Breck et al. |
| 2,996,358 A | 8/1961 | Milton |
| 3,001,869 A | 9/1961 | Longstreth et al. |
| 3,008,803 A | 11/1961 | Milton |
| 3,010,789 A | 11/1961 | Milton |
| 3,012,853 A | 12/1961 | Milton |
| 3,044,482 A | 7/1962 | Golden |
| 3,054,657 A | 9/1962 | Breck et al. |
| 3,130,007 A | 4/1964 | Breck |

(Continued)

FOREIGN PATENT DOCUMENTS

CA  614495  2/1961

(Continued)

OTHER PUBLICATIONS

Daniels, F. et al., "Absorption of Gases", Experimental Physical Chemistry, 1970, pp. 369-374, Seventh Edition, McGraw-Hill, no month.

(Continued)

*Primary Examiner*—Wayne A. Langel
(74) *Attorney, Agent, or Firm*—Christopher J. Cronin (57) ABSTRACT

Compositions comprising a reactive gas and a matrix gas are disclosed, as well as articles of manufacture and methods of making the articles. The methods of manufacturing preferably employ zeolites to remove moisture from the reactive gas and from the matrix gas, and then combine the moisture reduced gases either in a container, or prior to filling a container, which has been previously vacuum-baked and passivated. The invention produces stable standard gas compositions having improved shelf-life.

10 Claims, 2 Drawing Sheets

U.S. PATENT DOCUMENTS

| | | | |
|---|---|---|---|
| 3,140,249 A | 7/1964 | Plank et al. | |
| 3,140,252 A | 7/1964 | Frilette et al. | |
| 3,140,253 A | 7/1964 | Plank et al. | |
| 3,260,582 A | 7/1966 | Zimmer, Jr. et al. | |
| 3,638,464 A | 2/1972 | Winter et al. | |
| 3,688,453 A | 9/1972 | Legacy et al. | |
| 3,780,163 A | 12/1973 | Callighan et al. | |
| 3,834,200 A | 9/1974 | Winter | |
| 3,847,551 A | 11/1974 | Hutson | |
| 3,850,589 A | 11/1974 | Charvat | |
| 3,982,359 A | 9/1976 | Elbel et al. | |
| 4,049,396 A | 9/1977 | Hiles | |
| 4,057,510 A * | 11/1977 | Crouch et al. | 252/372 |
| 4,082,834 A | 4/1978 | Grossman et al. | |
| 4,135,130 A | 1/1979 | Wootton | |
| 4,137,151 A | 1/1979 | Csicsery | |
| 4,159,917 A | 7/1979 | Gluck | |
| 4,221,572 A | 9/1980 | Torimae et al. | |
| 4,227,350 A | 10/1980 | Fitzer | |
| 4,351,743 A | 9/1982 | Hashimoto | |
| 4,358,627 A | 11/1982 | Ameen et al. | |
| 4,414,128 A | 11/1983 | Goffinet | |
| 4,459,779 A | 7/1984 | Shen | |
| 4,485,519 A | 12/1984 | Collier | |
| 4,613,345 A | 9/1986 | Thicke et al. | |
| 4,622,253 A | 11/1986 | Levy | |
| 4,669,163 A | 6/1987 | Lux et al. | |
| 4,713,224 A | 12/1987 | Tamhankar et al. | |
| 4,724,819 A | 2/1988 | Fleri | |
| 4,781,907 A * | 11/1988 | McNeill | 423/351 |
| 4,853,148 A | 8/1989 | Tom et al. | |
| 4,902,561 A | 2/1990 | McCullough, Jr. et al. | |
| 4,923,828 A | 5/1990 | Gluck et al. | |
| 4,925,646 A | 5/1990 | Tom et al. | |
| 4,927,432 A | 5/1990 | Budinger et al. | |
| 4,931,358 A | 6/1990 | Wahl et al. | |
| 4,933,373 A | 6/1990 | Moren | |
| 4,935,295 A | 6/1990 | Serafini | |
| 4,991,362 A | 2/1991 | Heyer et al. | |
| 5,011,512 A | 4/1991 | Wald et al. | |
| 5,025,596 A | 6/1991 | Heyer et al. | |
| 5,062,900 A | 11/1991 | Berneron et al. | |
| 5,080,822 A | 1/1992 | VanEenam | |
| 5,080,831 A | 1/1992 | VanEenam | |
| 5,120,512 A | 6/1992 | Masuda | |
| 5,176,782 A | 1/1993 | Ishibashi et al. | |
| 5,197,852 A | 3/1993 | Walker et al. | |
| 5,203,189 A | 4/1993 | Lovejoy et al. | |
| 5,232,467 A | 8/1993 | Child et al. | |
| 5,250,085 A | 10/1993 | Mevisson | |
| 5,255,445 A | 10/1993 | Li et al. | |
| 5,273,558 A | 12/1993 | Nelson et al. | |
| 5,296,821 A | 3/1994 | Petersen et al. | |
| 5,363,604 A | 11/1994 | Heyer | |
| 5,479,727 A | 1/1996 | Fine et al. | |
| 5,480,677 A | 1/1996 | Li et al. | |
| 5,503,778 A | 4/1996 | Liu et al. | |
| 5,573,710 A | 11/1996 | McDonell | |
| 5,676,762 A | 10/1997 | Kimura et al. | |
| 5,880,850 A | 3/1999 | McAndrew et al. | |
| 5,910,292 A | 6/1999 | Alvarez, Jr. et al. | |
| 5,963,336 A | 10/1999 | McAndrew et al. | |
| 6,054,379 A | 4/2000 | Yau et al. | |
| 6,110,258 A | 8/2000 | Fraenkel et al. | |
| 6,154,284 A | 11/2000 | McAndrew et al. | |
| 6,183,539 B1 | 2/2001 | Rode et al. | |
| 6,255,222 B1 | 7/2001 | Xia et al. | |
| 6,318,640 B1 | 11/2001 | Coffee | |
| 6,325,304 B1 | 12/2001 | Brite et al. | |
| 6,328,223 B1 | 12/2001 | Holt et al. | |
| 6,328,543 B1 | 12/2001 | Benecke | |
| 6,332,562 B1 | 12/2001 | Sweeton | |
| 6,334,578 B1 | 1/2002 | House | |
| 6,345,404 B1 | 2/2002 | Stephens et al. | |
| 6,345,773 B1 | 2/2002 | Shanklin et al. | |
| 6,346,201 B1 | 2/2002 | Felkner | |
| 6,348,227 B1 | 2/2002 | Caracciolo, Jr. | |
| 6,395,070 B1 | 5/2002 | Bhadha et al. | |
| 6,444,326 B1 | 9/2002 | Smith | |
| 6,511,760 B1 | 1/2003 | Barone et al. | |
| 6,752,852 B1 * | 6/2004 | Jacksier et al. | 95/117 |
| 6,866,142 B1 * | 3/2005 | Lamborne et al. | 206/0.6 |

FOREIGN PATENT DOCUMENTS

| | | |
|---|---|---|
| CA | 616981 | 3/1961 |
| CA | 817915 | 7/1969 |
| EP | 0 492 868 A1 | 7/1992 |
| EP | 0517575 A | 12/1992 |
| GB | 1245373 | 9/1971 |
| JP | 53-100979 A | 9/1978 |
| JP | 63-057543 A | 3/1988 |
| JP | 62-49765 A | 9/1994 |
| WO | WO 92/01536 | 2/1992 |

OTHER PUBLICATIONS

Brunauer, S. et al., "Absorption of Gases in Multimolecular Layers", J.Am.Chem.Soc., 1938, 60 , pp. 309-316, no month.

Wechter, S.G., "Calibration in Air Monitoring—Preparation of Stable Pollution Gas Standards Using Treated Aluminum Cylinders", ASTM Special Technical Publication 598, 1975, pp. 40-54, no month.

Barrett, E.P., et al., "The Determination of Pore Volume and Area Distributions in Porous Substances", J.Am.Chem.Soc., Jan. 1951, 73, pp. 373-380.

Naffin, B. et al., "Removal of Harmful Acid Gases by Passage through Moistened Lime Filter Layers", Zement-Kalk-Gips Int'l, v. 49 n Sep. 9, 1996, 14pp.

* cited by examiner

REDUCED MOISTURE COMPOSITIONS COMPRISING AN ACID GAS AND A MATRIX GAS, ARTICLES OF MANUFACTURE COMPRISING SAID COMPOSITIONS, AND PROCESSES FOR MANUFACTURING SAME

CROSS REFERENCE TO RELATED APPLICATIONS

This application is related to non-provisional patent application Ser. Nos. 10/157,466 pending and 10/157,467 (now U.S. Pat. No. 6,752,852) both filed concurrently herewith on May 29, 2002, all of which are incorporated by reference herein.

BACKGROUND OF THE INVENTION

1. Field of the Invention

The invention is generally related to the field of manufacturing compositions comprising an acid gas and a matrix gas having reduced moisture, and which are stable in acid gas concentration for more than an insignificant time period. The invention is also related to articles of manufacture containing these compositions, such as metal cylinders containing the compositions, ton units containing the compositions, and the like.

2. Related Art

Moisture is known to react with reactive gases, such as the so-called "acid gases", for example, hydrogen sulfide, carbonylsulfide, carbondisulfide and mercaptans (mercaptans are also referred to as thiols) to form a complex compound. (The term "acid gas" is used herein to denote either gas phase, liquid phase, or mixture of gas and liquid phases, unless the phase is specifically mentioned.)

One problem presents itself: if one is interested in producing reactive gas standard compositions, in other words reactive gases having a known concentration of one of these gases in a matrix or carrier fluid, then one must consider how to reduce or remove the moisture. Gas standards may have to have, and preferably do have, a long shelf life, since the standard reactive gas may not be required immediately after production. A source of reactive gas may contain a considerable amount of moisture. Therefore, the reduction or removal of moisture from the reactive gas is of primary importance if the stability of the reactive gas in the standard gas is to be maintained. It has also recently been observed that moisture in the matrix gas (prior to its being mixed with the acid gas) contributes to the problem, for if one removes moisture from the reactive gas, and then mixes the dried reactive gas with a wet matrix gas, the problem has not been entirely solved, even if the moisture level in the matrix gas is comparatively low.

A second, related problem involves the containers that the reactive gas standards are stored in. If metal or metal lined, reactive gases will react with and/or become adsorbed onto the metal, and will ultimately change the concentration of the reactive gas.

Grossman et al. (U.S. Pat. No. 4,082,834) describes alloys, such as alloys of nickel, titanium, and zirconium, that react with water and reactive gases (such as hydrogen, hydrogen-containing compounds such as hydrocarbons, carbon monoxide, carbon dioxide, oxygen, and nitrogen) at temperatures ranging from about 200° C. to about 650° C. While the patent does not discuss acid gases, it is apparent that hydrogen sulfide, carbonyl sulfide, and mercaptans are hydrogen-containing compounds, so that there would not be any expected benefits using these alloys to remove moisture from these acid gases. While carbondisulfide does not contain hydrogen, and therefore there could be some moisture reduction from a composition comprising carbondisulfide and moisture using these alloys, the high temperature is prohibitive for commercial use.

Tamhankar et al. (U.S. Pat. No. 4,713,224) describes a one-step process for removing minute quantities of impurities from inert gases, where the impurities are selected from the group consisting of carbon monoxide, carbon dioxide, oxygen, hydrogen, water and mixture thereof. The process comprises contacting the gas with a particulate material comprised of nickel in an amount of at least about 5% by weight as elemental nickel and having a large surface area, from about 100 to about 200 $m^2/g$. There is no disclosure of removal of moisture from reactive gases; there is therefore no discussion or suggestion of moisture removal from reactive gases, moisture removal from matrix gases and mixing same to form a standard gas composition.

Tom et al (U.S. Pat. Nos. 4,853,148 and 4,925,646) discloses processes and compositions for drying of gaseous hydrogen halides of the formula HX, where X is selected from the group consisting of bromine, chlorine, fluorine, and iodine. The patent describes the use of, for example, an organometallic compound such as an alkylmagnesium compound, on a support. The halide is substituted for the alkyl functional group. Suitable supports are, alumina, silica, and aluminosilicates (natural or synthetic). However, there is no description or suggestion of reducing or removing moisture from sulfur-containing reactive gases, or of removal of moisture from matrix gases and mixing the reduced moisture gases to form a standard gas. Alvarez, Jr. et al. (U.S. Pat. No. 5,910,292) describes a process and apparatus for removal of water from corrosive halogen gases, using a high silica zeolite, preferably high silica mordenite. The patent describes removing moisture down to less than or equal to 100 ppb water concentration in halogen gases, particularly chlorine- or bromine-containing gases, but once again, there is lacking any teaching of suggestion of standard gas compositions. U.S. Pat. No. 6,183,539 discloses utilizing high sodium, low silica faujasite particles for the adsorption of carbon dioxide and water vapor from gas streams. The disclosed types of gas streams in which this type of high sodium, low silica faujasite crystals can be utilized includes air, nitrogen, hydrogen, natural gas, individual hydrocarbons and monomers, such as ethylene, propylene, 1,3 butadiene, isoprene and other such gas systems. There is no mention of sulfur-containing acid gas purification using the faujasites, or production of standard gas compositions.

U.S. Pat. No. 4,358,627 discloses use of "acid resistant" molecular sieves, such as that known under the trade designation "AW300", for reducing the chloride concentration in chlorinated liquid hydrocarbons that contain an ethylenically unsaturated chlorinated hydrocarbon, water and hydrogen chloride. The method includes providing certain nitrogen-containing compounds in the system and contacting the system with the molecular sieve. There is no disclosure or suggestion, however, of removal or reduction of moisture from gas phase compositions, or production of standard gas compositions.

Given the problems of moisture reacting with sulfur-containing acid gases and other reactive gases, and the fact that some or all reactive gases will react with metals, there is a definite and unmet need for standard gas compositions, articles of manufacture including those standards which are stable over reasonable periods of time, and methods of producing same.

SUMMARY OF THE INVENTION

The present invention overcomes many if not all of the problems noted above. In accordance with the present invention, certain "acid gas resistant" molecular sieve compositions are employed to reduce or remove moisture from fluid compositions comprising a reactive gas (preferably an acid gas, preferably a sulfur-containing acid gas), and moisture is removed from a matrix gas using the same or different means. The reduced moisture reactive gas and reduced moisture matrix gas are then combined, either prior to entering a vacuum-baked, "passivated" container, or added to the vacuum-baked, passivated container in succession, or added simultaneously (for example through separate valves) where mixing takes place in the container. As used herein the term "remove" means that the water content of the final composition comprising the reactive gas will be equal to or less than 100 parts per billion (ppb), more preferably less than 10 ppb, and more preferably less than 1 ppb. As used herein the term "reduced" means that the moisture concentration of the final composition comprising the reactive gas will be no more than 0.1 times the starting fluid composition water concentration, preferably no more than 0.01 times, and more preferably no more than 0.001 times the starting moisture concentration. Presently, the detection limit for moisture is about 4 ppm in reactive gases comprising a sulfur-containing compound. Compositions are made to 4 ppm concentration, then diluted to the desired reduced moisture concentration. As used herein the term "sulfur-containing compound" includes carbondisulfide, carbonylsulfide, and compounds within formula (I):

wherein S is sulfur,
X and Y are the same or different and are independently selected from the group consisting of hydrogen, alkyl, aryl, oxygen, and alcohol.

Examples of preferred sulfur-containing compounds within formula (I) include hydrogen sulfide, sulfur dioxide, methylthiol, ethylthiol, n-propylthiol, i-propylthiol, benzylthiol, and the like.

In accordance with the present invention, methods of passivating internal surfaces of containers that have been cleaned and vacuum-baked are employed to increase the shelf-life of gas compositions, especially low concentration reactive gas products. As used herein the term "shelf-life" means that time during which the initial concentration of a reactive gas stored in a container is substantially maintained at the intended or desired concentration. In this context, the phrase "substantially maintained" means that for concentrations of about 1000 parts per billion (ppb), the reactive gas concentration does not vary by more than +/−10 percent; for concentrations of about 500 ppb, the concentration does not vary by more than +/−15 percent; for concentrations of about 100 ppb, the concentration does not vary by more than +/−20 percent. "Low concentration" reactive gases means gases having a concentration in another gas, such as inert gas or matrix gas, of 1000 ppb or less.

The passivated internal metal surface of the container comprises (1) the reaction product of a silicon-containing material and an oxygen-containing material (preferably selected from the group consisting of moisture, molecular oxygen, metal oxides, and mixtures thereof), and (2) an effective amount of the reactive gas, the effective amount being many times the intended concentration of reactive gas that is to be substantially maintained. Preferred articles of manufacture of the invention include products wherein the passivated internal surface is a passivated metal. Preferably the metal is selected from the group consisting of aluminum, aluminum alloys, steel, iron and combinations thereof. Yet other preferred manufactured products of the invention are those wherein the silicon-containing material is selected from the group consisting of compounds within the general formula (II):

wherein $R^1$, $R^2$, $R^3$, and $R^4$ are the same or different and are independently selected from the group consisting of hydrogen, halogen, amine, alkyl, aryl, halogenated alkyl, and halogenated aryl; and manufactured products wherein the compound is silane or a methyl-containing silane, more preferably wherein the methyl-containing silane is selected from the group consisting of methylsilane, dimethylsilane, trimethylsilane and tetramethylsilane.

Reactive gases which benefit from the passivation techniques of the present invention include nitrous oxide, nitric oxide, hydrogen chloride, chlorine, boron trichloride, and any acid gases except those that would react with a silicon-containing compound.

A first aspect of the invention are compositions comprising a reactive gas (preferably an acid gas, preferably a sulfur-containing compound) and a matrix gas, wherein the sulfur-containing compound has a concentration in the composition of no more than 1 part per million (ppm) in the matrix gas, and the composition has a moisture concentration of no more than 100 ppm, preferably no more than 10 ppm, more preferably no more than 1 ppm. Preferred compositions are those wherein the reactive gas is selected from the group consisting of nitrous oxide, nitric oxide, hydrogen chloride, chlorine, boron trichloride, and any acid gases except those that would react with a silicon-containing compound, including sulfur-containing compounds selected from the group consisting of carbondisulfide, carbonylsulfide, and compounds within formula (I).

A second aspect of the invention are articles of manufacture comprising:
a) a container having an internal space and a passivated internal metal surface;
b) a composition of the first aspect of the invention contained within the internal space and in contact with the passivated internal metal surface, the reactive gas having an intended concentration that is substantially maintained; and
c) the passivated internal metal surface comprising:
  1) the reaction product of a silicon-containing material and an oxygen-containing material (preferably selected from the group consisting of moisture, molecular oxygen, metal oxides, and mixtures thereof), and
  2) an effective amount of the reactive gas, the effective amount being many times the intended concentration of reactive gas that is to be substantially maintained.

Preferred articles of manufacture of the invention are those wherein the reactive gas is selected from those mentioned in the first aspect of the invention. Other preferred articles of manufacture include products wherein the passivated internal surface is a passivated metal. Preferably the metal is selected from the group consisting of aluminum, aluminum alloys, steel, iron and combinations thereof. Yet other preferred manufactured products of the invention are those wherein the silicon-containing material is selected from the group consisting of compounds within the general formula (II).

Preferred articles of manufacture of the invention are those wherein the composition comprises a reactive gas having a concentration of about 1000 ppb and that does not vary by more than +/−10 percent; products wherein the composition comprises a reactive gas having a concentration of about 500 ppb and that does not vary by more than +/−15 percent; products wherein the composition comprises a reactive gas having a concentration of about 100 ppb and that does not vary by more than +/−20 percent. Products wherein the composition comprises higher or lower concentration of reactive gas, and correspondingly larger or smaller variation in concentration, are considered within the invention.

Preferred articles of manufacture of the invention comprise only a single reactive gas with an inert gas like nitrogen, argon, helium, and the like. The composition may comprise a mixture of two or more reactive gases. Also, the balance of the fluid composition is, in some preferred embodiments, a hydrocarbon, such as ethylene, propylene, and the like.

A third aspect of the invention are methods of making articles of manufacture of the invention, the methods comprising the steps of:

i) reducing the moisture content of a reactive gas (preferably an acid gas, preferably a sulfur-containing gas) using an acid-gas resistant molecular sieve, to form a reduced moisture reactive gas;

ii) reducing the moisture content of a matrix gas using means for moisture reduction, to form a reduced moisture matrix gas;

iii) vacuum baking an internal metal surface of a container (preferably including any metal surfaces of metal valves attached to the container) at a temperature ranging from about 30° C. to about 75° C. for no less than 1 hour (preferably no less than 6 hours, more preferably no less than 12 hours), at a vacuum no more than 100 torr, preferably no more than 1 torr, and more preferably no more than 0.01 torr, to form a vacuum-baked internal metal surface of the container;

iv) exposing the vacuum-baked internal metal surface of the container to a first fluid composition comprising a silicon-containing compound for a time sufficient to allow at least some of the silicon-containing compound to react with oxygen-containing compounds (preferably selected from the group consisting of moisture, molecular oxygen, metal oxides, and mixtures thereof) present to form a silicon-treated surface on at least some of the vacuum-baked internal metal surface of the container, the silicon-containing compound preferably selected from the group consisting of compounds within the general formula (II);

v) evacuating the container for a time sufficient to remove substantially all of the silicon-containing compound(s) that has not reacted with the oxygen-containing compounds to form the silicon-treated surface;

vi) exposing the silicon-treated surface to a second fluid composition, the second fluid composition comprising a reactive gas having a concentration that is greater than an intended reactive gas concentration of the article of manufacture;

vii) evacuating the container for a time sufficient to remove just enough of the second fluid composition to enable maintenance of an increased shelf-life, low concentration reactive gas at the intended concentration in the container; and viii) combining at least a portion of the reduced moisture reactive gas with at least a portion of the reduced moisture matrix gas to form an intended gas composition in the container.

Preferred methods in this aspect of the invention are those wherein the silicon-containing compound is selected from the group consisting of silane, methylsilane, dimethylsilane, trimethylsilane and tetramethylsilane. Also preferred are methods wherein the second fluid composition has a concentration of reactive gas at least 10 times the intended reactive gas concentration of the manufactured product; methods wherein steps iv) and v) are repeated prior to step vi); methods wherein the metal surface is cleaned prior to step iii); methods wherein the concentration of the silicon-containing compound used in step vi) ranges from about 100 ppm to 100 percent; and methods wherein during step vii) the second composition is heated to a temperature of not more than 75° C. Other preferred methods are those wherein the container is a gas cylinder having an attached cylinder valve, and the cylinder valve is removed prior to step iv). After steps i)–vi) are completed, preferably at very high temperatures for steps iv) and vi, the cylinder valve is reattached, and the process steps iv)–vi) are repeated, but steps iv) and vi) take place at not more than 75° C.

Preferred acid gas-resistant molecular sieve is selected from the group consisting of molecular sieves having an effective pore size ranging from about 1 Angstrom up to about 10 Angstroms, more preferably ranging from about 3 to about 8 Angstroms. Preferred are the molecular sieves known under the trade designations AW300 and AW500, particularly herein the molecular sieve is AW300.

Preferably, moisture removal steps within the invention are carried out at combinations of temperature and flow rate that will ensure water in the fluid will not freeze, and where the reactive gas will not decompose. Preferred temperatures range from just above 0° C. to just below a temperature where the reactive gas will decompose. Temperatures below 0° C. are disfavored because of the possibility of water freezing in the container, or in the molecular sieve pores, or both. Temperatures above the decomposition temperature of the reactive gas during moisture removal are disfavored due to possible decomposition of the reactive gas. It may be possible, through increased flow rate (or decreased residence time) conditions in the container, to operate below 0° C. or exceed the decomposition temperature briefly. Generally, it is preferred to operate at reduced temperature, as the acid gas resistant molecular sieve materials seem to operate more efficiently at these temperatures.

Further aspects and advantages of the invention will become apparent by reviewing the description of preferred embodiments that follow.

DESCRIPTION OF PREFERRED EMBODIMENTS

Adsorption of moisture from fluid compositions comprising moisture and sulfur-containing compounds may be evaluated through several theories, with the exception that such theories do not recognize the benefits of use of an acid gas-resistant molecular sieve. The degree of adsorption of moisture onto the acid gas-resistant adsorbent depends in a complicated way on the chemical and physical properties of the adsorbent, the temperature and pressure employed during this step, as well as on the chemical and physical properties of the particular sulfur-containing fluid from which moisture is being removed. These parameters are in turn dictated by the final concentration of moisture in the sulfur-containing fluid that is to be produced.

A discussion of adsorption of gaseous species onto surfaces that is helpful in this respect is included in Daniels, F. et al., "Experimental Physical Chemistry", Seventh Edition, McGraw-Hill, pages 369–374 (1970). While the inventors are not certain, it is believed that the attraction of the reactive gas to the coating is physical in nature, involving an interaction of dipoles or induced dipoles, but may be chemical in nature involving chemical bonds, as when oxygen is adsorbed on charcoal. A combination of physical and chemical forces may be at work as well.

As stated in Daniels, et al., infra, experimental data for adsorption may be plotted as adsorption isotherms, in which the quantity of gas adsorbed (expressed as milliliters at 0° C. and 760 mm) per gram of adsorbing material is plotted against the equilibrium pressure. In many cases of adsorption it is possible to relate the amount of adsorbed material to the equilibrium pressure, using the empirical equation of Freundlich, $$V = kP^n$$

where

V=number of milliliters of gas, corrected to 0° C. and 760 mm, adsorbed per gram of adsorbing material;

P=pressure; and k and n are constants that may be evaluated form the slope and intercept of the line obtained when log V is plotted against log P.

Alternatively, Langmuir considered adsorption to distribute molecules over the surface of the adsorbent in the form of a unimolecular layer. Consideration of the dynamic equilibrium between adsorbed and free molecules leads to the following relation:

$$P/V = P/V_u + 1/kV_u$$

Where P and V are as defined previously, $V_u$ is the volume of gas 0° C., 760 mm adsorbed per gram adsorbent when unimolecular layer is complete, and k is a constant characteristic of the adsorbent-adsorbate pair. Thus, if P/V is plotted against P, a straight line is obtained if the Langmuir equation applies. The slope of the line is equal to 1/Vu; when the line is extrapolated to low pressures, as P goes to 0, P/V approaches the finite limit 1/kVu. The values of the constants may also be obtained by plotting 1/V versus 1/P. By postulating the building up of multimolecular adsorption layers on a surface, Brunauer, Emmett, and Teller extended the Langmuir derivation for unimolecular layer adsorption to obtain an isotherm equation for the more complicated case. Thus, the surface area of a coating produced by the practice of the present invention may be determined by the B.E.T. method, and preferably is at least about 1 m²/gram, more preferably at least 10 m²/gram. If the coating is somewhat porous, the pore volume may be determined by nitrogen adsorption isotherm methods, and is preferably at least 0.1 ml/gram. The B.E.T. method is described in detail in Brunauer, S. Emmet, P. H., and Teller, E., J. Am. Chem. Soc., 60, 309–16 (1938). The nitrogen adsorption isotherm method is described in detail in Barrett, E. P., Joyner, L. G. and Helenda, P. P., J. Am. Chem. Soc., 73, 373–80 (1951), incorporated by reference herein.

As stated previously, the term "remove" means that the water content of the final composition comprising the sulfur-containing compound will be equal to or less than 100 ppb, more preferably less than 10 ppb, and more preferably less than 1 ppb. (As noted previously, these moisture concentrations are not presently measurable directly, but are obtained by dilution.) As used herein the term "reduce" means that the moisture concentration of the final composition comprising the sulfur-containing fluid will be no more than 0.1 times the starting fluid composition water concentration, preferably no more than 0.01 times, and more preferably no more than 0.001 times the starting moisture concentration.

The acid gas resistant molecular sieves useful in the invention are typically and preferably those described in Ameen et al. (U.S. Pat. No. 4,358,627), incorporated by reference herein. Preferred are the acid gas resistant molecular sieves known under the trade designations AW 300 and AW 500, available from Universal Oil Products (UOP). The effective pore size of the molecular sieve known under the trade designation AW 300 is about 4 Angstroms, and the effective pore size of the molecular sieve known under the trade designation AW 500 is about 5 Angstroms. A discussion of the acid gas resistant molecular sieves may be found in Collins, J. J., "A Report on Acid-Resistant Molecular Sieve Types AW-300 and AW-500", Oil and Gas Journal, Dec. 2, 1963, which is incorporated herein by reference. Such molecular sieves are available as pellets of diameters of about one eighth inch and one sixteenth inch.

As stated in U.S. Pat. No. 4,358,627, molecular sieves are crystalline metal alumino-silicates. The molecular sieves are basically a 3-dimensional framework of $SiO_4$ and $AlO_4$ tetrahedra, the tetrahedra being cross-linked by the sharing of oxygen atoms so that the ratio of oxygen atoms to the total of the aluminum and silicon atoms is equal to 2. The electro valance of the tetrahedra containing aluminum is balanced by the inclusion in the crystal of a cation, for example an alkali or alkaline earth metal ion. One cation may be exchanged for another by ion exchange techniques, which are known. The spaces between the tetrahedra are occupied by water molecules prior to dehydration. The dehydration results in crystals interlaced with channels of molecular dimensions that offer very high surface areas for the adsorption of foreign molecules. In addition, the term "molecular sieve" as used in the present disclosure contemplates not only aluminosilicates, but also substances in which the aluminum has been partly or wholly replaced, such as for instance by gallium and/or other metal atoms, and further includes substances in which all or part of the silicon has been replaced, such as for instance by germanium. Titanium and zirconium substitution may also be practiced. Most molecular sieves, or zeolites as they are also referred to, are prepared or occur naturally in the sodium form, so that sodium cations are associated with the electro negative sites in the crystal structure. However, the molecular sieve may be ion exchanged. Suitable cations for replacement of sodium in the molecular sieve crystal structure include ammonium (decomposable to hydrogen), hydrogen, rare earth metals, alkaline earth metals, and the like. Various suitable ion exchange procedures and cations which may be exchanged into crystal structure are well known to those skilled in the art. Examples of the naturally occurring crystalline aluminosilicate zeolites which may be used or included in the present invention are faujasite, mordenite, clinoptilote, chabazite, analcite, erionite, as well as levynite, dachiardite, paulingite, noselite, ferriorite, heulandite, scolccite, stibite, harmotome, phillipsite, brewsterite, flarite, datolite, gmelinite, caumnite, leucite, lazurite, scaplite, mesolite, ptholite, nepheline, matrolite, offretite and sodalite. Examples of the synthetic alumino-silicate zeolites which are useful for carrying out the present invention are Zeolite X, U.S. Pat. No. 2,882,244, Zeolite Y, U.S. Pat. No. 3,130,007; and Zeolite A, U.S. Pat. No. 2,882,243; as well as Zeolite B, U.S. Pat. No. 3,008,803; Zeolite D, Canada Pat. No. 661,981; Zeolite E, Canada Pat. No. 614,495; Zeolite F, U.S. Pat. No. 2,996,358; Zeolite H, U.S. Pat. No. 3,010,789; Zeolite J, U.S. Pat. No. 3,001,869; Zeolite L, Belgian Pat. No. 575,177; Zeolite M, U.S. Pat. No. 2,995,423, Zeolite 0, U.S. Pat. No. 3,140,252; Zeolite Q, U.S. Pat. No. 2,991,151; Zeolite S, U.S. Pat. No. 3,054,657, Zeolite T, U.S. Pat. No. 2,950,962; Zeolite W, U.S. Pat. No. 3,012,853, Zeolite Z, Canada Pat. No. 614,495; and Zeolite Omega, Canada Pat. No. 817,915. Also ZK-4HJ, alpha beta and ZSM-type zeolites are useful. Moreover, the zeolites described in U.S. Pat. Nos. 3,140,249, 3,140,253, 3,044,482 and 4,137,151 are also useful, the disclosures of said patents being incorporated herein by reference.

Figure 1:
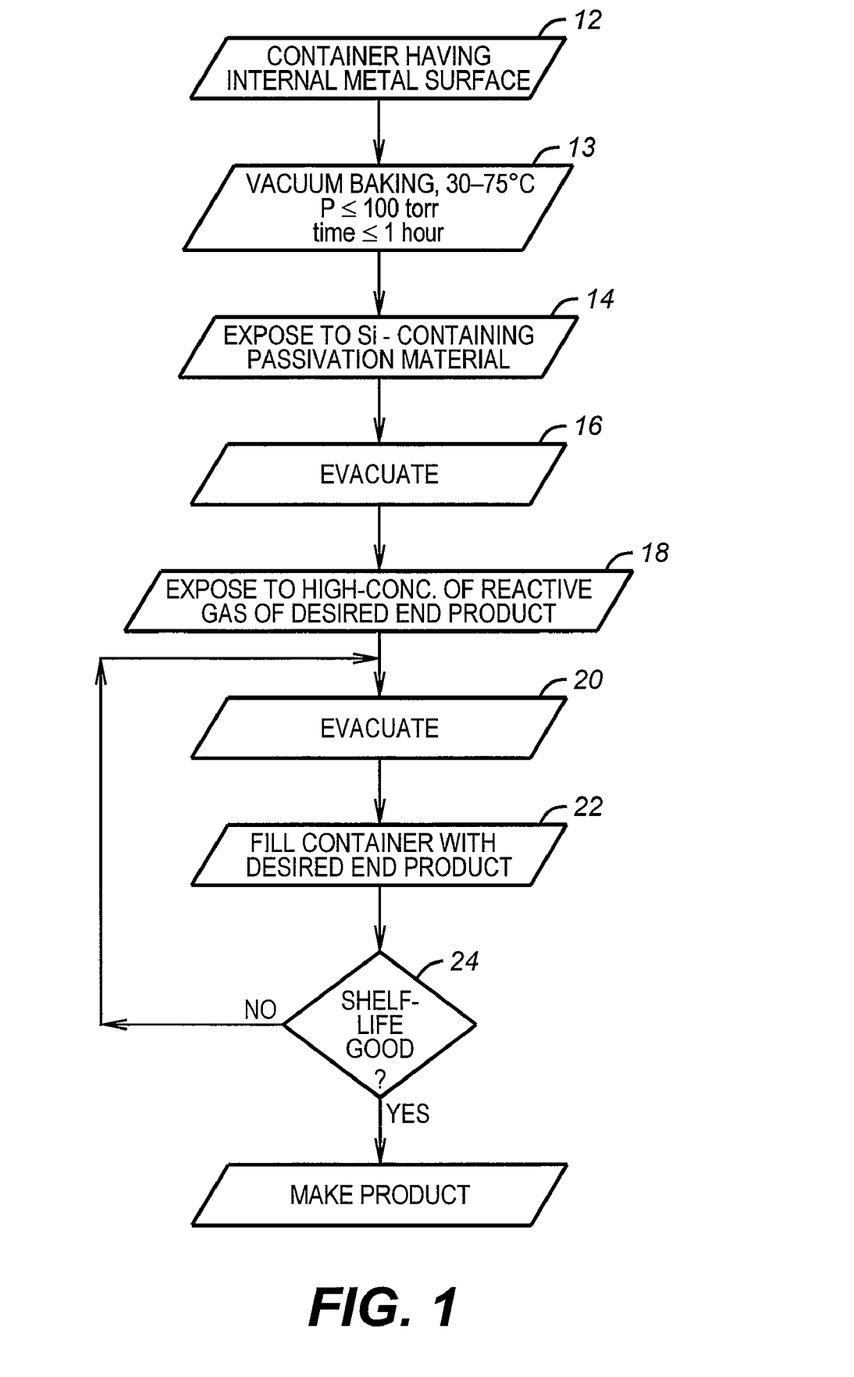
FIG. 1 is a logic diagram illustrating the methods of the invention.

Referring now to FIG. 1, there is illustrated schematically a logic diagram for carrying out methods of the invention. A container having a metal internal surface is selected at 12. The metal surface is vacuum baked, in step 13, at temperatures ranging from about 30° C. to about 75° C., at reduced pressure, preferably no more than 100 torr, more preferably no more than 1 torr, more preferably no more than 0.01 torr, for a time of no less than 1 hour, preferably no less than 6 hours, and more preferably no less than 12 hours. This forms a vacuum-baked internal metal surface, which is then exposed to a silicon-containing passivation material, 14, for a time and at a temperature and pressure sufficient to react most of the silicon-containing material with oxygen-containing compounds present on the metal surface. Step 14 individually is a known passivation technique, typically combined with nitrogen baking, and needs little explanation to the skilled artisan. See for example "Wechter on Stable Pollution Gas Standards", p. 44, ASTM (1976). The container is then evacuated for a time sufficient to remove the bulk of the non-reacted silicon-containing material, at 16. Next, the metal surface is exposed to high concentration of reactive gas or liquid of the desired end product to be contained in the container, at 18. Step 18 is also known as an alternative passivation technique to Step 14, and needs little explanation to the skilled artisan. See "Wechter on Stable Pollution Gas Standards", p. 43–44, ASTM (1976). The container is again evacuated at 20 for a time sufficient to remove substantially all of the non-adsorbed reactive gas. The container is then ready to be filled at 22, either with the composition having the desired material at the desired concentration of moisture and reactive gas, or with a reduced moisture matrix gas and a reduced moisture reactive gas, or first with a reduced moisture matrix gas and then with a reduced moisture reactive gas, or first with a reduced moisture reactive gas and then with a reduced moisture matrix gas. At this point, the container is allowed to equilibrate and the concentration of the gas in the container is tested at various times to determine the concentration of reactive gas in the container. If the shelf life is acceptable at 24, the product is made in accordance with the procedure followed, at 26. If the concentration of the gas increases or decreases beyond the accepted tolerances, then the process of steps 20, 22, and 24 are repeated. Optionally, steps 14 and 16 may be repeated, as indicated at 26.

Moisture may be removed from reactive gases as taught in co-pending Ser. No. 10/157,467, now U.S. Pat. No. 6,752,852, filed simultaneously with the present application. The co-pending application describes an apparatus comprising a fluid inlet end, a fluid outlet end, a container, and an acid gas resistant molecular sieve contained within an internal space within container. The container may take any shape required by the user, including cylindrical, kidney shaped, spiral wound, and the like. Preferably the container is cylindrical. The fluid outlet end may have a connection to a conduit which preferably routes some or all of the effluent fluid, reduced in moisture content, to a means for moisture measuring, preferably a diode laser-based sensor, as described in U.S. Pat. Nos. 5,880,850; 5,963,336; and 6,154,284, all incorporated herein by reference. Such sensors typically include one or more diode laser sources, temperature control circuits, and the like, and a spectroscopic cell through which the diode laser passes through and encounters all or a portion of the gas sample being analyzed. Through an analysis of the absorbed radiation by the species of interest, in this case moisture, the concentration of the species of interest may be determined. Similar apparatus and moisture sensors are preferably employed to remove moisture from matrix gases. In practice, a source of reactive gas, such as a tank or truck trailer, or other source of fluid such as cylinder or ton unit are provided. A ton unit may be a source liquid or a source of gas. In any case, fluid comprising a reactive gas and moisture enter a means for removing moisture as described in reference to co-pending application Ser. No. 10/157,467, now U.S. Pat. No. 6,752,852. The means for moisture removal may have a spare unit or units installed in parallel. A bypass conduit allows one container to be taken out of service and replaced, if necessary. Fluid depleted in moisture exits the container, and then is either mixed with the reduced moisture matrix gas, or delivered straight to the vacuum-baked, passivated container. Optionally, the moisture-depleted reactive fluid may be passed through a downstream treatment unit, which is preferably a unit that removes particulate matter that may have escaped from the molecular sieve. An optional temperature control unit is preferred. As a general rule, the acid gas resistant molecular sieves seem to work more efficiently at cooler temperatures (25° C. and lower), although one must be careful not to freeze the moisture being removed. Also, there may be temperatures above 25° C. at which chemisorption contributes significantly to the overall adsorption, due to higher kinetic rate constants at higher temperatures. However, as temperature is increased even more, this effect will tend to be overcome by the physical desorption of moisture from the molecular sieve.

The means for maintaining the molecular sieve in the container is a material that is substantially inert to the acid gas. Preferably, the means for maintaining the molecular sieve in the container is the molecular sieve material itself contacting an inner surface of the container. For economic reasons, it may be preferred to hold the acid gas-resistant molecular sieve in a secondary or material inside the container, such as with end screens in the fluid entrance and exit ends made from porous metals such as stainless steels, aluminum, VCR connections, gaskets, frits, and the like. Further it may be preferred to mix the acid gas-resistant molecular sieve with one or more non-acid gas-resistant materials, preferably another molecular sieve material. It is within the invention to use more than one container, either in parallel or series arrangement in terms of flow of feed fluid. For example, it may be desired to have a series arrangement, where the second or succeeding containers have the same or different molecular sieve materials. In parallel arrangements, it is preferred to have two containers with the same molecular sieve in each container, and to effect flow in one container while the other container is being regenerated, such as by heating, contacting with dry fluid, or combination of these. Such parallel and series arrangements are known in the adsorption art, for example, the air separation field.

Reduced moisture compositions of the invention preferably comprising a reduced moisture reactive gas and a reduced moisture matrix gas, the compositions comprising at least one reactive gas having a reactive gas concentration and a moisture concentration, the moisture concentration being no more than 0.1 times the concentration of the reactive gas in the matrix gas. Fluid compositions may either have one reactive gas, or more than one. If more there are two reactive gases, the molar ratio of the two may range from about 1:99 to about 99:1, more preferably from about 20:80 to about 80:20, and more preferably ranging from about 40:60 to about 60:40. Examples of fluid compositions considered within the invention include a mixture of carbonylsulfide and hydrogen sulfide in a nitrogen matrix gas, the molar ratio of carbonylsulfide to hydrogen sulfide ranging from about 20:80 to about 80:20; mixtures of hydrogen sulfide and methylthiol (otherwise known as methyl mercaptan) in a nitrogen matrix gas, with molar ratio of hydrogen sulfide to methylthiol ranging from about 20:80 to about 80:20, and the like.

During the moisture removal steps, the flow rate of the fluid comprising moisture (either a reactive gas or a matrix gas) will be sufficient to create a space velocity preferably of at least one container volume per minute, more preferably at least about 5 container volumes per minute. It is also possible, although not preferred, to mix moist reactive gases with moist matrix gases, and then remove the moisture from both the reactive gas and the matrix gas simultaneously. However, it is believed to be more controllable, and therefore more preferable, to remove moisture separately from reactive gases and matrix gases. The space velocity of course will depend on the temperature of the feed fluid, the amount of moisture in the feed fluid, the flow pattern through the apparatus of the invention. If the fluid is gaseous, higher temperatures and higher flow rates will tend to create more difficulty in removing moisture from the fluid, as the volume of the fluid will tend to be larger and there will be less contact time. Conversely, in general lower temperatures and lower feed rates will be beneficial in removing more moisture. The feed pressure is not critical, but it should not be so high as to render the pressure drop through the container too high, lest the molecular sieve be damaged. Preferably, a means for filtering the product fluid is provided (downstream of the molecular sieve) to filter out and particles of molecular sieve that may break away form the main portion.

Figure 2:
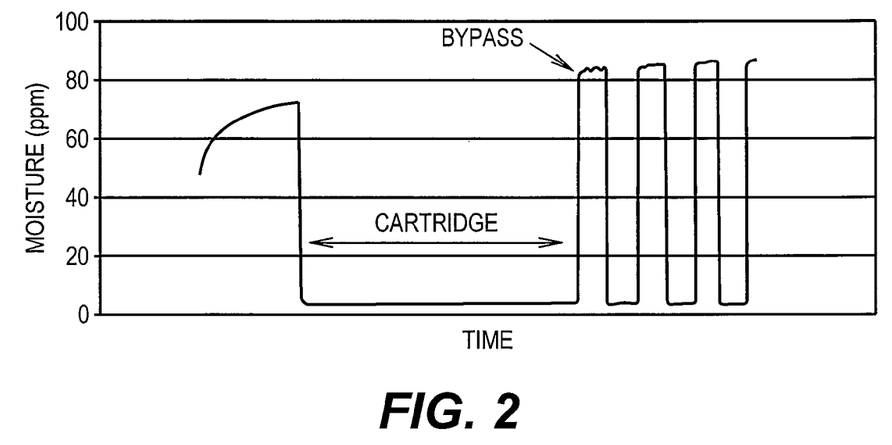
FIG. 2 is a graph illustrating moisture removal data from hydrogen sulfide (reactive gas) in one embodiment of the invention.

FIG. 2 is a graph illustrating moisture removal data from hydrogen sulfide in one embodiment of the invention. The apparatus comprised 14 grams of the molecular sieve known under the trade designation AW300, which had flowing there through a gas stream comprising hydrogen sulfide and from about 60 to about 80 ppm of moisture. The test was conducted at room temperature (about 20° C.). The flow rate of the gas stream through the molecular sieve was 1 liter/minute. The moisture in the stream exiting the apparatus was measured using a diode laser measurement system, such as described in U.S. Pat. Nos. 5,880,850; 5,963,336; and 6,154,284, previously incorporated herein by reference, although other means for moisture analysis could be used as well. As may be seen in the data of FIG. 2, the molecular sieve worked extremely well in reducing the moisture level of the hydrogen sulfide stream.

Additional experiments were performed on sulfur dioxide streams, and similar moisture removal abilities were observed.

Figure 3:
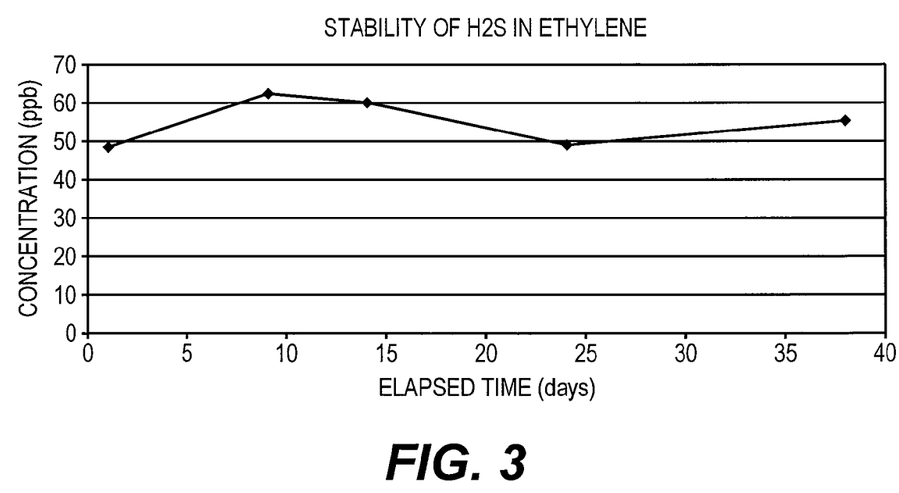
FIG. 3 illustrates stability data for a standard mixture of 1 ppm $H_2S$, which had been previously de-moisturized as described in reference to FIGS. 2, mixed with a purchased ethylene matrix gas originally having 1 ppm moisture, and after vacuum-baking an aluminum cylinder at 65° C. at a vacuum of 1 torr for 6 hours.

FIG. 3 illustrates 38 days of stability data for a standard mixture of 1 ppm $H_2S$, which had been previously de-moisturized as described in reference to FIG. 2, mixed with a purchased ethylene matrix gas (ethylene purity 99.99995, from Special Gas Services originally having 1 ppm moisture), and after vacuum-baking an aluminum cylinder at 65° C. at a vacuum of 1 torr for 6 hours. As may be seen, the stability of the mixtures are quite good after this time period. Although this data was obtained using purchased ethylene matrix gas having a reduced moisture, it is expected that the same or very similar results would be obtained upon using a "wet" mixture of a reactive gas with a matrix gas, and then de-moisturizing the mixture and placing the de-moisturized mixture into a passivated container in accordance with the invention, or taking separate sources of "wet" reactive gas and "wet" matrix gas, de-moisturizing each separately, then mixing in a passivated container.

Although the description herein is intended to be representative of the invention, it is not intended to limit the scope of the appended claims.

What is claimed is:

1. An article of manufacture comprising:
   a) a container having an internal space and a passivated internal metal surface;
   b) a composition contained within the internal space and in contact with the passivated internal metal surface, wherein
      i) the composition comprises a reactive gas and a matrix gas,
      ii) the reactive gas has a concentration in the composition of no more than 1 part per million in the matrix gas, the concentration being substantially maintained, and
      iii) the composition has a moisture concentration of no more than 100 ppm; and
   c) the passivated internal metal surface comprising:
      1) the reaction product of a silicon-containing material and an oxygen-containing material, and
      2) an amount of the reactive gas adsorbed on the reaction product, the amount resultant from previous exposure of the reaction product to a high concentration of the reactive gas before evacuation of the high concentration reactive gas from the internal space prior to filling the internal space with the composition, the high concentration of the reactive gas before evacuation being many times the concentration of reactive gas that is being substantially maintained.

2. The article of manufacture of claim 1 wherein the reactive gas has a concentration of about 500 ppb, and the concentration does not vary by more than +/−15 percent.

3. The article of manufacture of claim 1 wherein the reactive gas has a concentration of about 100 ppb, and the concentration does not vary by more than +/−20 percent.

4. The article of manufacture of claim 1 wherein the oxygen-containing material is selected from the group consisting of moisture, molecular oxygen, metal oxides, and mixtures thereof.

5. The article of manufacture of claim 1 wherein the passivated metal is selected from the group consisting of aluminum, aluminum alloys, steel, iron and combinations thereof.

6. The article of manufacture of claim 1 wherein the silicon-containing material is selected from the group consisting of compounds within the general formula (II):

$$SiR^1R^2R^3R^4 \qquad (II)$$

wherein $R^1$, $R^2$, $R^3$, and $R^4$ are the same or different and are independently selected from the group consisting of hydrogen, halogen, amine, alkyl, aryl, halogenated alkyl, and halogenated aryl.

7. The article of manufacture of claim 6 wherein the silicon-containing compound is selected from the group consisting of silane, dimethylsilane, trimethylsilane, tetramethylsilane, and mixtures thereof.

8. The article of manufacture of claim 1 wherein the matrix gas selected from the group consisting of nitrogen, argon, helium, and mixtures thereof.

9. The article of manufacture of claim 1 comprising a mixture of two or more reactive gases in a matrix gas.

10. The article of manufacture of claim 1 wherein the gas composition comprises a hydrocarbon.

* * * * *